United States Patent
Gotch et al.

(10) Patent No.: US 8,999,169 B2
(45) Date of Patent: Apr. 7, 2015

(54) METHOD OF DETERMINING A PHOSPHORUS BINDER DOSAGE FOR A DIALYSIS PATIENT

(75) Inventors: Frank A. Gotch, San Francisco, CA (US); Benjamin J. Lipps, Boston, MA (US); Peter Kotanko, New York, NY (US); Nathan W. Levin, New York, NY (US); Amanda K. Stennett, Waltham, MA (US); Norma J. Ofsthun, Lexington, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 962 days.

(21) Appl. No.: 12/580,803

(22) Filed: Oct. 16, 2009

(65) Prior Publication Data

US 2010/0096330 A1   Apr. 22, 2010

Related U.S. Application Data

(60) Provisional application No. 61/196,420, filed on Oct. 17, 2008.

(51) Int. Cl.
*B01D 61/34* (2006.01)
*A61K 31/785* (2006.01)
*A61K 31/00* (2006.01)
*A61K 33/06* (2006.01)
(Continued)

(52) U.S. Cl.
CPC .............. *A61K 31/785* (2013.01); *A61K 31/00* (2013.01); *A61K 33/06* (2013.01); *A61K 45/06* (2013.01); *G01N 33/84* (2013.01)

(58) Field of Classification Search
None
See application file for complete search history.

(56) References Cited

U.S. PATENT DOCUMENTS

| 5,753,706 A | 5/1998 | Hsu |
| 2002/0183288 A1 | 12/2002 | Mazess et al. |

(Continued)

FOREIGN PATENT DOCUMENTS

| DE | 101 28 511 A1 | 9/2004 |
| EP | 1 932 808 A1 | 6/2008 |
| WO | WO 2008/134518 A2 | 11/2008 |

OTHER PUBLICATIONS

Toussaint et al., "Review of dialysate calcium concentratoin in hemodialysis", Hemodialysis International vol. 10 (2006), pp. 326-337.*

(Continued)

*Primary Examiner* — Dirk Bass
(74) *Attorney, Agent, or Firm* — Hamilton, Brook, Smith & Reynolds, P.C.

(57) ABSTRACT

The invention is directed to a method of determining a dosage of phosphorus binder for a patient undergoing dialysis treatment to achieve a pre-dialysis serum phosphorus concentration within a desired concentration range while achieving a desired net accumulation of calcium. The method includes determining the dosage of phosphorus binder that will achieve pre-dialysis serum phosphorus concentration of the patient that is within the desired concentration range while accounting for the change in the amount of phosphorus removed by the dialysis treatment when the pre-dialysis serum phosphorus concentration of the patient is within the desired concentration range, determining a dialysate calcium concentration that will result in the desired net accumulation of calcium over a complete dialysis cycle, and dialyzing the patient with a dialysate containing a calcium concentration based upon that determination.

6 Claims, 9 Drawing Sheets

(51) Int. Cl.
*A61K 45/06* (2006.01)
*G01N 33/84* (2006.01)

(56) References Cited

U.S. PATENT DOCUMENTS

2004/0043971 A1 3/2004 Mazess et al.
2006/0115430 A1 6/2006 Cantor

OTHER PUBLICATIONS

Gotch, "Calcium and Phosphorus Kinetics in Hemodialysis Therapy", Contributions in Nephrology vol. 161 (2008), pp. 210-214.*

Nishi, H., et al., "Control of Parathyroid Function in Patients with a Short History of Hemodialysis," *Therapeutic Apheresis and Dialysis*, vol. 9, No. 1, pp. 39-43 (2005) (No month available).

Fukagawa, M., et al., "Cinacalcet (KRN1493) Effectively Decreases the Serum Intact PTH Level with Favourable Control of the Serum Phosphorus and Calcium Levels in Japanese Dialysis Patients," *Nephrol Dial Transplant*, vol. 23, pp. 328-335 (2008) (No month available).

Notification of Transmittal of the International Search Report and the Written Opinion of the International Searching Authority, or the Declaration for International Application No. PCT/US2009/061009, 18 pp., mailed Jan. 18, 2010.

International Preliminary Report on Patentability and Written Opinion, PCT/US2009/061009, date of mailing Apr. 28, 2011.

* cited by examiner

METHOD OF DETERMINING A PHOSPHORUS BINDER DOSAGE FOR A DIALYSIS PATIENT

RELATED APPLICATION

This application claims the benefit of U.S. Provisional Application No. 61/196,420, filed on Oct. 17, 2008.

The entire teachings of the above application are incorporated herein by reference.

BACKGROUND OF THE INVENTION

Soft tissue calcification is a major cause of morbidity and mortality in dialysis patients. This calcification of soft tissue is believed to be due to excess amounts and/or accumulation of calcium and phosphorus in the body. See G. R. Bailie, *Calcium and Phosphorus management in chronic kidney disease: Challenges and trends,* 39 Formulary pp. 358-365 (2004). Vascular calcification is particularly problematic in dialysis patients as it associated with myocardial dysfunction, heart failure, and cardiac arrest. Id.

Generally, plasma calcium concentrations are maintained within very narrow limits (typically between about 1.1 and about 1.3 mmol/L). See J. T. Daugirdas, P. G. Blake, and T. S. Ing, *Handbook of Dialysis,* (2007). Hormonally, calcium levels are regulated by parathyroid hormone (PTH), which is secreted by the parathyroid glands in response to a decrease in ionized calcium ($Ca^{2+}$) below its normal range. PTH stimulates the movement of calcium and its counterion phosphorus from the bone to the blood and extracellular fluid (ECF) and further increases calcium resorption and phosphorus excretion by the kidney. Calcium levels are also controlled by intake of vitamin $D_3$, which increases calcium and phosphorus absorption by the intestines, the primary site in regulating dietary calcium absorption. The intake of vitamin $D_3$ can be from dietary sources or from vitamin $D_3$ analogs, such as, for example, calcitriol (e.g, Rocaltrol®), doxercalciferol (e.g., Hectorol®), or paricalcitol (e.g., Zemplar®). Ionized calcium levels that are too low result in hyperexcitability and tetanic convulsions whereas ionized calcium levels that are too high can cause death due to muscle paralysis and coma.

Despite the importance in regulating calcium levels during hemodialysis, how to control calcium balance in dialysis patients is poorly understood. In patients having chronic renal failure, both net calcium absorption and calcium intake are generally reduced, however, as discussed above, the use of IV Vitamin $D_3$ increases calcium absorption. In addition, the failure in the glomerular filtration rate (GFR) of the kidney leads to a decrease in urinary calcium excretion. Thus, decreased excretion causes patients with end-stage renal disease (ESRD) to typically have positive serum calcium mass balances.

Similarly, phosphorus accumulates in patients with renal insufficiency due to lack of excretion of phosphorus by the kidney and this excess phosphorus is often not sufficiently eliminated by dialysis treatments. Consequently, nearly all ESRD patients develop hyperphosphatemia. Id. An additional complication caused by elevated levels of serum phosphorus is increased calcium-phosphorus (Ca×P) product, that must be maintained below a threshold value of 55 $mg^2/dL^2$ in order to prevent precipitation of calcium phosphate and calcification of vascular, cardiac, and other soft tissues. Id. To remove excess phosphorus, however, patients are generally given phosphate binders, such as calcium acetate or calcium carbonate, and these calcium containing compounds further add to the calcium load in the patients. Still, calcium levels must be maintained within normal concentrations as low ionized calcium levels can lead to hypotension, decreased myocardial contractility, and aggravation of secondary hypoparathyroidism.

Despite the need to control a hemodialysis patient's intradialytic calcium and phosphorus mass balances to account for the patient's interdialytic calcium and phosphorus mass balances, there has heretofore not been a satisfactory method for doing so. One problem in doing so, for example, is that a patient's interdialytic calcium and phosphorus accumulation or depletion cannot be accurately determined by simply measuring the patient's serum calcium concentration before a hemodialysis treatment. This is because, for example, physiological regulation of serum calcium maintains the serum calcium concentration within a narrow range which is not indicative of the patient's interdialytic calcium mass balance.

In the past 20 years, a similar problem in assessing the adequacy of dialysis has been addressed by urea kinetic modeling (UKM). Modeling was necessary because a low concentration of urea in the blood after a dialysis treatment could be the result of either poor nutritional intake or adequate dialysis. See National Kidney Foundation Clinical Practice Guidelines for Hemodialysis Adequacy, *American Journal of Kidney Diseases*, Vol 30 (3) Suppl. 2 (1997). The standard measure of dialysis adequacy is called Kt/V, a dimensionless quantity composed of K, the dialyzer's rate of clearance of a substance from the patient's blood, typically measured in mL/min, the total time of the dialysis treatment, typically measured in minutes, and the volume of distribution of that substance in the patient's body, typically measured in liters (and converted to mL). A typical value of Kt/V for adequate dialysis is about 1.2, which, for a given patient (constant V) can be achieved by a dialysis treatment for a longer time (larger t), or a higher efficiency dialyzer (higher K). The substance chosen as a marker of dialysis adequacy was urea. See F. G. Casino, and T. Lopez, *The equivalent renal urea clearance. A new parameter to assess dialysis dose,* Nephrol. Dial. Transplant., Vol. 11 pp. 1574-1581 (1996).

Urea is the major end product of protein catabolism, making up about 90% of waste nitrogen accumulating in body water between dialysis treatments. While urea itself is not particularly toxic, its concentration is easily calculated from a blood urea nitrogen (BUN) measurement, and therefore it was adopted as an index for measuring the adequacy of dialysis. The BUN is a concentration, typically expressed in mg/dL, however, and therefore the other variable required to obtain the grams of urea is the volume of distribution of urea in the patient's body. The volume of distribution is obtained from urea kinetic modeling (UKM), which takes into account the movement of urea from poorly perfused areas (such as the arms and legs) to the extracellular space, after dialysis has been completed. This volume of distribution is termed double pool or equilibrated volume of distribution, and the end result is termed the equilibrated protein catabolic rate (ePCR). See T. Depner, and J. Daugirdas, *Equations for normalized protein catabolic rate based on two-point modeling of hemodialysis urea kinetics,* Journal of the American Society of Nephrology, Vol. 7 (5), pp. 780-785 (1996).

There is a need to apply the kinetic modeling approach to phosphorus management, to quantify the amount of phosphorus and calcium absorbed by the patient from their diet as well as the amount removed by dialysis treatment and phosphorus binder dosage, so that dialysis treatment parameters and medication prescriptions can be tailored to the needs of an individual patient. This approach will be termed phosphorus kinetic modeling (PKM).

SUMMARY OF THE INVENTION

The invention is directed to a method of determining a dosage of phosphorus binder for a patient undergoing dialysis treatment to achieve a pre-dialysis serum phosphorus concentration within a desired concentration range while achieving a desired net accumulation of calcium. The method includes determining the dosage of phosphorus binder that will achieve a pre-dialysis serum phosphorus concentration of the patient that is within the desired concentration range while accounting for the change in the amount of phosphorus removed by the dialysis treatment when the pre-dialysis serum phosphorus concentration of the patient is within the desired concentration range, determining a dialysate calcium concentration that will result in the desired net accumulation of calcium over a complete dialysis cycle, and dialyzing the patient with a dialysate containing a calcium concentration based upon that determination. In some embodiments, the patient has at least one disease or condition selected from the group consisting of renal insufficiency, renal failure, kidney disease, hyperphosphatemia, hypercalcemia, hypocalcemia, end-stage renal disease, and cancer.

In certain embodiments, the dialysate calcium concentration can be determined from a calcium mass balance over the complete dialysis cycle. In some specific embodiments, the desired net accumulation of calcium is approximately zero.

In some embodiments, the desired range for the pre-dialysis serum phosphorus concentration of the patient is between about 3.5 mg/dL and about 5.5 mg/dL. In certain embodiments, the dialysate calcium concentration is determined by considering additional patient safety considerations in changing the dialysate calcium concentration from one dialysis treatment to the next.

Thus, this invention provides a mechanism to understand and control the magnitude of calcium and phosphorus accumulation and removal in patients undergoing renal replacement therapy to optimize calcium balance at desired levels in these patients. An ability to quantitatively estimate total calcium and phosphorus transport in such a patient would allow clinicians and other medical personnel to adjust calcium and phosphorus mass balances during and/or between dialysis treatments to prevent potentially undesired accumulation or depletion of calcium and/or phosphorus.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

The primary steps in management of phosphorus and calcium metabolism for a patient undergoing periodic dialysis treatments using the methods of this invention typically include: (1) quantitatively assess a patient's interdialytic intake of calcium and phosphorus, including a quantitative assessment of a patient's absorption of calcium and phosphorus, given the patient's dosage of vitamin $D_3$ analogs such as, for example, calcitriol, Hectorol®, or Zemplar®, and the patient's dosage of phosphate binder, such as, for example, calcium acetate (e.g., PhosLo® (667 mg dose, Fresenius Medical Care, Waltham, Mass.)) or calcium carbonate, or sevelamer hydrochloride (e.g., Renagel® (800 mg dose, Genzyme Corp., Cambridge, Mass.)), or combinations thereof that will achieve a pre-dialysis serum phosphorus concentration of the patient that is within the desired concentration range while accounting for the change in the amount of phosphorus removed by the dialysis treatment when the pre-dialysis serum concentration of the patient is within the desired concentration range, (2) determining a desired calcium mass balance for the patient over a complete dialysis cycle, (3) calculating an intradialytic calcium mass balance, (4) calculating an intradialytic phosphorus mass balance, and (5) utilizing the phosphorus kinetic model (PKM) to determine the desired calcium concentration of the dialysate solution used in the dialysis treatment to achieve the desired calcium mass balance over a complete dialysis cycle, in order to control accumulation of calcium and inhibit vascular calcification and mortality.

As defined in this application, the interdialytic calcium mass balance of a patient takes into account the amount of calcium absorbed by the patient between dialysis treatments, and the intradialytic calcium mass balance takes into account the amount of calcium that is exchanged between the patient's blood and the dialysate solution during a particular dialysis treatment session. As defined in this application, periodic dialysis treatments are performed typically several days apart, typically three times per week, but the time period between treatments is not necessarily constant. A consistent three times per week schedule results in two 2-day interdialytic periods and one 3-day interdialytic period, typically over the weekend. Furthermore, occasionally the patient can receive treatment after a shorter time period since the last treatment when the patient needs to shed excess fluid.

The methods of this invention apply to human patients that are undergoing dialysis treatment due to their having a disease or condition that affects kidney function such as, for example, renal insufficiency, renal failure, kidney disease, hyperphosphatemia, hypercalcemia, hypocalcemia, end-stage renal disease, and cancer. The dialysis treatment of the patient is a treatment that replaces or supplements the normal function of the kidneys of a patient.

Figure 1:
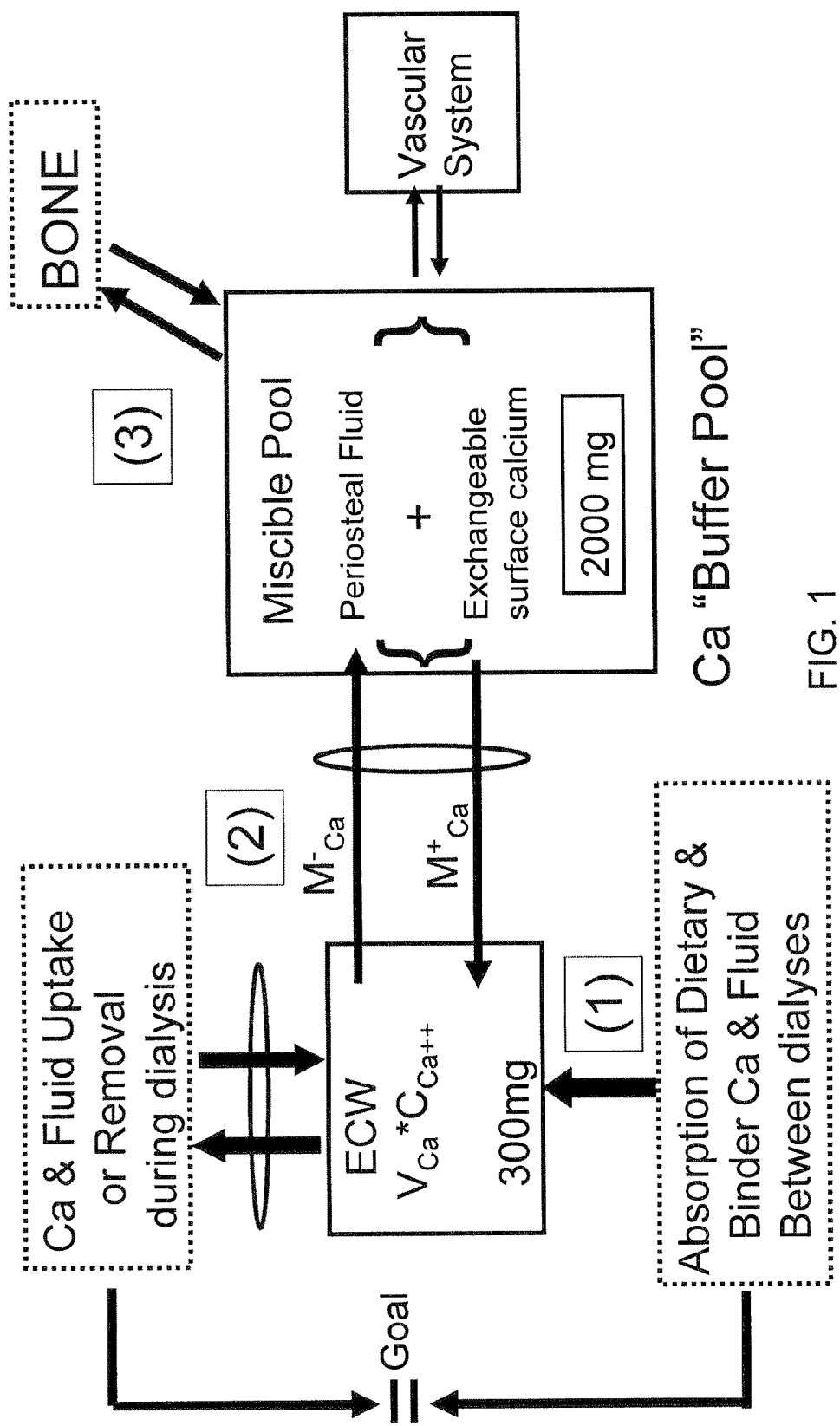
FIG. 1 is a block diagram representation of the three components of calcium mass balance in a patient.

Between dialysis treatments, a patient usually takes in calcium and phosphorus from dietary sources, such as dairy products, and, in the case of phosphorus, protein and soft drink intake. A prescribed intake of phosphate ($PO_4$) binders, which are usually calcium acetate (e.g., PhosLo® (667 mg dose, Fresenius Medical Care, Waltham, Mass.)) or calcium carbonate, or sevelamer hydrochloride (e.g., Renagel® (800 mg dose, Genzyme Corp., Cambridge, Mass.)), or combinations thereof, that are prescribed to achieve a pre-dialysis phosphorus concentration in the patient's blood of between about 3.5 and about 5.5 mg/dL, preferably about 4.5 mg/dL, can also affect the patient's serum calcium level. The phosphate binder converts the phosphorus ingested by the patient into a bound (phosphate) form that cannot be absorbed and is therefore eliminated from the patient's body. The amount of calcium absorbed by the patient into his or her body can also be affected by a prescribed amount of a vitamin $D_3$ analog, such as, for example, calcitriol, Hectorol®, or Zemplar®. As shown in FIG. 1, the distribution volume of ionized calcium in the patient's body is the volume of extracellular water (ECW). A patient's body will maintain the serum ionized ($Ca^{+2}$) calcium concentration in the patient's blood within normal or near normal levels, which are generally between about 4.6 mg/dL and about 5.3 mg/dL, more preferably from about 4.8 to about 5.2 mg/dL, by exchanging calcium with a miscible calcium pool, composed of the patient's periosteal fluid and exchangeable surface calcium on the patient's bone surfaces.

Between dialysis treatments, a patient's blood will also usually accumulate excess fluid, which is removed by convection during the dialysis treatment in order to prevent swelling and edema, usually in the patient's ankles and lower extremities. The excess fluid often enters the patient's body with a near zero calcium concentration. The patient's body uses calcium from the miscible calcium pool, to the extent that the amount of calcium absorbed by the patient from dietary or prescribed sources of calcium is insufficient, to raise the calcium concentration in the excess fluid to normal or near normal levels. During the dialysis treatment, the excess fluid leaves the body of the patient while containing the normal or near normal concentration of calcium, and therefore the patient's miscible calcium pool will be depleted of that amount of calcium. It is desirable to prevent the depletion of the patient's miscible calcium pool, because, without wishing to be bound by any particular theory, it is believed that repeated cycles of depletion lead to loss of calcium in the bones of the patient, and consequent bone embrittlement.

Figure 2:
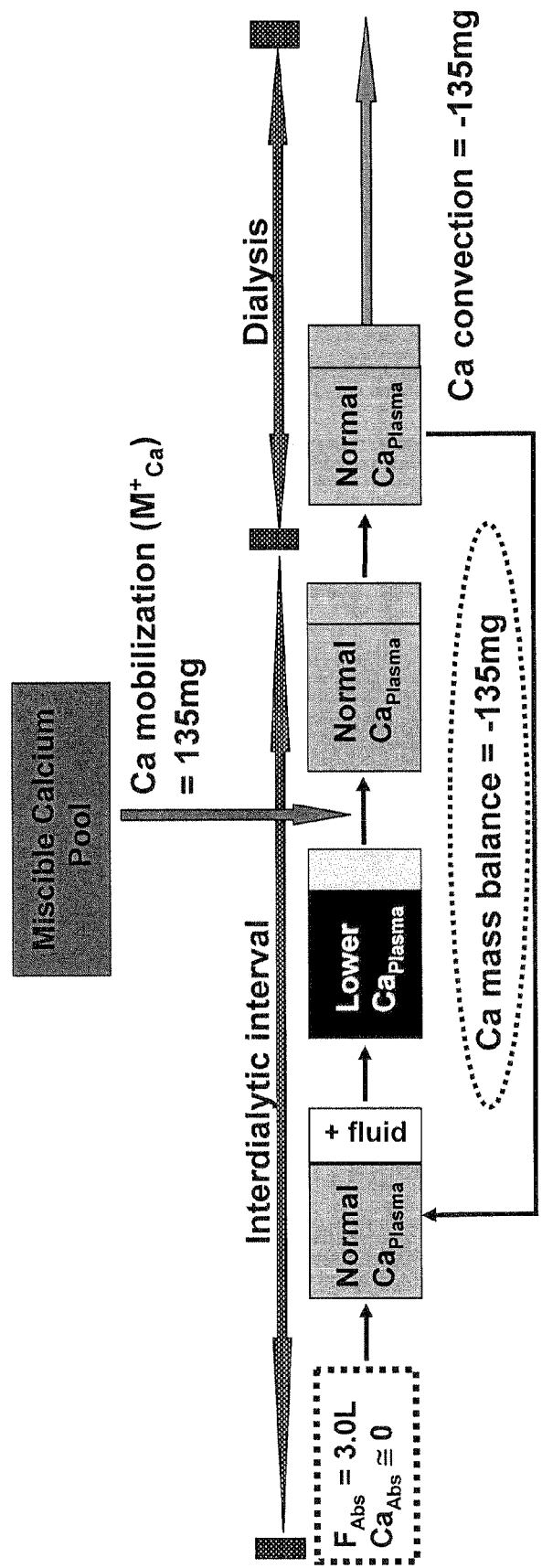
FIG. 2 is a block diagram representation of calcium distribution in a patient under negative calcium mass balance conditions ($Ca_{Abs} \ll F_{Abs}$), over a complete dialysis cycle.

As shown in FIG. 2, the methods of this invention also enable a clinician skilled in the art to determine a concentration of dialysate solution that is sufficiently higher than the concentration of calcium in the patient's blood to create a positive diffusion gradient across the dialyzer membrane and therefore a positive intradialytic mass balance while taking into account the amount of calcium containing fluid removed. In this way, an amount of calcium is added by diffusion of calcium to the patient's blood from the dialysate solution, leading to a desired calcium mass balance over a complete dialysis cycle, usually zero or near zero.

A patient that has absorbed calcium from the dietary or medically prescribed sources discussed above will typically have added an amount of calcium, usually measured in milligrams (mg), to his or her miscible calcium pool (MCP). For many patients, it is desirable to achieve a zero or near zero calcium mass balance over a complete dialysis cycle, which encompasses the interdialytic period and the intradialytic treatment period, by removing that amount of calcium accumulated between dialysis treatments from the patient's blood. This prevents the calcium-phosphorus product from exceeding the threshold level for vascular calcification. In the case of some patients, particularly those suffering from osteoporosis, it is desirable to achieve a positive intradialytic calcium mass balance, thus adding to the calcium content of the miscible calcium pool and the osteoporosis patient's bone surfaces, while removing a amount of phosphorus sufficient to prevent calcium phosphate product from exceeding the threshold level, thus preventing vascular calcification. The determination of the amount of positive intradialytic calcium mass balance that is desirable for a patient suffering from osteoporosis is a qualitative determination made by a physician skilled in the art.

Figure 3:
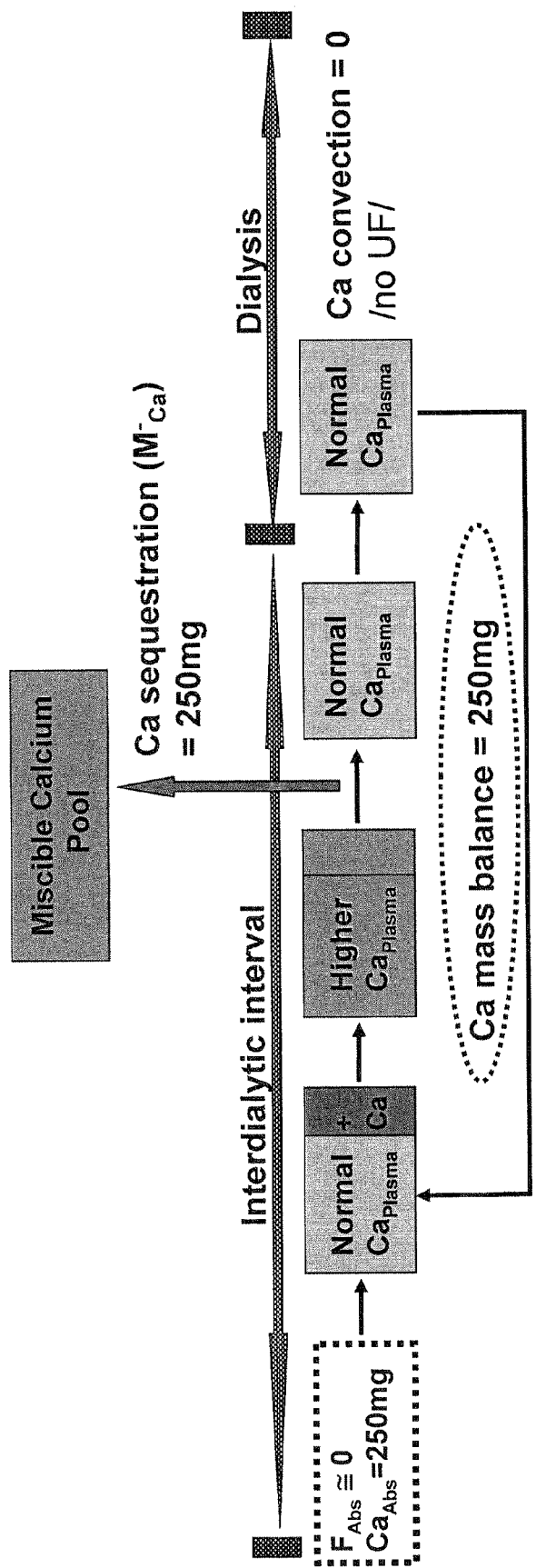
FIG. 3 is a block diagram representation of calcium distribution in a patient under positive calcium mass balance conditions ($Ca_{Abs} \gg F_{Abs}$), over a complete dialysis cycle.

As shown in FIG. 3, the methods of this invention enable a clinician skilled in the art to determine a concentration of calcium in a dialysate solution that is sufficiently lower than the concentration of calcium in the patient's blood to create a negative diffusion gradient across the dialyzer membrane and therefore a negative intradialytic mass balance, so that an amount of accumulated calcium is removed by diffusion of calcium from the patient's blood into the dialysate solution, leading to a desired calcium mass balance over a complete dialysis cycle, usually zero or near zero. A negative intradialytic calcium mass balance leads to a short term reduction in the serum concentration of calcium in the patient's blood, before the patient's miscible calcium pool supplies an amount of calcium that is sufficient to restore the patient's serum concentration of calcium to normal or near normal levels. A patient with an expected negative intradialytic mass balance is usually prescribed a calcium mimetic, such as, for example, cinacalcet (e.g., Sensipar®), in order to prevent the secretion of parathyroid hormone (PTH), called in the art a syndrome of inappropriate PTH secretion, which would otherwise stimulate the movement of calcium from the patient's bones into the patient's blood, leading to undesirable bone loss and embrittlement.

In many cases, the standard prescribed dialysate solution has a calcium concentration of about 2.5 mg/dL. In a substantial fraction of patients, the results of the model related to the methods of this invention have shown that it is desirable to use for the dialysis treatment a lower dialysate concentration of calcium than the standard concentrations used in many cases. The lower concentrations are typically between about 2.0 and about 2.5 mg/dL, and more preferably between about 2.0 and about 2.25 mg/dL, although dialysate calcium concentrations as low as about 1.5 mg/dL could be used, because a substantial fraction of patients require a negative intradialytic calcium mass balance in order to achieve the desired calcium mass balance over a complete dialysis cycle, usually zero or near zero.

The change in total calcium in the miscible pool, Ca_MP, can be obtained from a calcium mass balance over a complete dialysis cycle from $$Ca\_MP = Ca\_HD - Ca\_HD\_C - Ca\_EC\_D \quad (1)$$

where Ca_HD, typically measured in mg, is the change in total calcium due to hemodialysis, Ca_HD_C, typically measured in mg, is the change in total calcium due to convection, and Ca_EC_D, typically measured in mg, is the change in total calcium in the extracellular space due to diffusion at constant volume.

The change in total calcium due to hemodialysis, Ca_HD, can be obtained from $$Ca\_HD = J\_Ca * T \quad (2)$$

where J_Ca, typically measured in mg/min, is the total flux of calcium during the dialysis treatment, and T, typically measured in minutes, is the total dialysis treatment time.

The total flux of calcium due to hemodialysis, J_Ca, can be obtained from $$J\_Ca = (D\_Ca*(1-Q\_f/Q\_pe)*(Dial\_Ca*2.0039 - C\_iCa\_m) - Q\_f*C\_iCa\_m)/100 \quad (3)$$

where D_Ca, typically measured in mL/min, is the dialysance of calcium (rate of clearance) of the dialyzer, Q_f, typically measured in mL/min, is the ultrafiltration rate of fluid during the dialysis treatment, Q_pe, typically measured in mL/min, is the effective plasma flow rate, Dial_Ca, typically measured in mEq/L, is the dialysate calcium concentration, C_iCa_m, typically measured in mg/dL, is the mean serum concentration of ionized calcium, and the value of 2.0039 is a conversion factor from mEq/L (milliequivalents per liter) to mg/dL, related to the atomic weight of calcium (40.078 grams/mol).

The dialysance of calcium, D_Ca, can be obtained from $$D\_Ca = Q\_pe*(1-\exp[(KoA\_Ca/Q\_pe)*(1-Q\_pe/Qd)])/(Q\_pe/Qd - \exp[(KoA\_Ca/Q\_pe)*(1-Q\_pe/Qd)]) \quad (4)$$

where KoA_Ca, typically measured in mL/min, is the dialyzer mass transfer coefficient for calcium, and Qd, typically measured in mL/min, is the dialysate flow rate.

The dialyzer mass transfer coefficient for calcium, KoA_Ca, can be obtained from $$KoA\_Ca = 332*\ln(Q\_pe) - 1409 \quad (5)$$

The effective plasma flow rate, Q_pe, can be obtained from $$Q\_pe = 2*Q\_p \quad (6)$$

where Q_p, typically measured in mL/min, is the plasma flow rate. The plasma flow rate, Q_p, can be obtained from $$Q\_p = Qb*(1 - HCT/100) \quad (7)$$

where Qb, typically measured in mL/min, is the blood flow rate through the dialyzer, and HCT, typically measured in percent, is the hematocrit count in the patient's blood. The hematocrit count is the percentage of formed elements, which are mostly (99%) red blood cells and also white blood cells and platelets, in the patient's blood. The hematocrit count is typically between about 30% and about 42% of blood by volume for dialysis patients.

The ultrafiltration rate, Q_f, can be obtained from $$Q\_f = UF\_t * 1000/T \quad (8)$$

where UF_t, typically measured in liters, is the total ultrafiltration volume, which is calculated from pre- and post-treatment weights and includes the total fluids administered during the treatment.

The mean serum concentration of ionized calcium, C_iCa_m, can be obtained from $$C\_iCa\_m = C\_iCa\_t - ((C\_iCa\_0 - C\_iCa\_t)/(0.012*T))*(\exp(-0.012*T) - 1) \quad (9)$$

where C_iCa_t, typically measured in mg/dL, is the post-treatment serum concentration of ionized calcium, and C_iCa_0, typically measured in mg/dL, is the pre-treatment serum concentration of ionized calcium.

The change in total calcium due to convection, Ca_HD_C, can be obtained from $$Ca\_HD\_C = -Q\_f*T*C\_iCa\_m/100 \quad (10)$$

The change in total calcium in the extracellular space due to diffusion at constant volume, Ca_EC_D, can be obtained from $$Ca\_EC\_D = (C\_iCa\_t - C\_iCa\_0)*V\_Ca\_t*10 \quad (11)$$

where V_Ca_t, typically measured in liters, is the post-treatment volume of distribution of calcium.

The post-treatment volume of distribution of calcium, V_Ca_t, can be obtained from $$V\_Ca\_t = Vol\_UKM/3 \quad (12)$$

where Vol_UKM, typically measured in liters, is the mean volume of distribution of urea, obtained from UKM.

The total amount of phosphorus removed from the patient, which should equal the patient's dietary intake of phosphorus, P_di, can be obtained from $$P\_di = (-P\_HD\_d/0.75) + 25*N\_PL + (186*\text{Ln}(Kru) + 72) \quad (13)$$

where P_HD_d, typically measured in mg, is the amount of phosphorus removed by the hemodialysis treatment, Kru, is the patient's residual renal clearance of urea, and N_PL is the number of PhosLo® phosphate binder pills (667 mg dose) initially prescribed to the patient. PhosLo® typically removes 25 mg of phosphorus per pill. The residual renal clearance of urea, Kru, can be calculated from measuring the volume of urine collected between dialysis treatments, the urine BUN concentration, and the pre- and post-dialysis treatment serum BUN concentrations. The residual renal clearance of urea, Kru, can be obtained from $$Kru = [(\text{Urine BUN})*(\text{urine volume})]/[(\text{average of (pre- and post-BUN)})*(\text{time between dialyses})] \quad (14)$$

The patient's residual renal clearance of urea, Kru, typically measured in mL/min, can be set to zero if it is unknown for a particular patient. The amount of phosphorus removed by the hemodialysis treatment, P_HD, can be obtained from $$P\_HD = (-(D\_P*(1-Q\_f/Q\_pw) + Q\_f)*C\_P\_m)*T/100 \quad (15)$$

where D_P is the dialysance of phosphorus of the dialyzer, typically expressed in mL/min, Q_pw is the plasma water flow rate, typically expressed in mL/min, and C_P_m is the mean serum phosphorus concentration, typically expressed in mg/dL.

The dialysance of phosphorus of the dialyzer can be obtained from $$D\_P = Q\_pw*(1-\exp[(300/Q\_pw)*(1-Q\_pw/Qd)])/(Q\_pw/Qd - \exp[(300/Q\_pw)*(1-Q\_pw/Qd)]) \quad (16)$$

where the dialyzer mass transfer coefficient for phosphorus, KoA_P, is equal to 300 mL/min.

The plasma water flow rate, Q_pw, can be obtained from $$Q\_pw = 0.94*Qb*(1 - HCT/100) \quad (17)$$

The mean serum phosphorus concentration, C_P_m, can be obtained from $$C\_P\_m = C\_P\_0*(1-(1-1.1*(C\_P\_t/C\_P\_0))*(1-\exp(-1.73*KtV\_P))) \quad (18)$$

where C_P_0 is the patient's serum phosphorus concentration pre-treatment, C_P_t is the patient's serum phosphorus concentration post-treatment, and KtV_P is the phosphorus dialysis adequacy of the dialyzer. Phosphorus in human serum, plasma, or urine can be quantitatively determined using an automated clinical chemistry analyzer. The method employed by the analyzer can be photometric. For example, inorganic phosphate will form an ammonium phosphomolybdate complex having the formula $(NH_4)_3 \ [PO_4(MoO_3)_{12}]$ with ammonium molybdate in the presence of sulfuric acid. The concentration of the complex can be determined photometrically in the ultraviolet region (340 nm). R. J. Henry, *Clinical Chemistry: Principles & Techniques*, $2^{nd}$ Ed. p. 723 (1974).

The KtV_P is a dimensionless measure of the effectiveness of phosphorus removal by dialysis. The KtV_P can be obtained from $$KtV\_P = ((D\_P*T)/(Vol\_UKM/3))/1000 \quad (19)$$

The daily average amount of phosphorus removed by hemodialysis, P_HD_d, can be obtained from $$P\_HD\_d = P\_HD*N\_tx/7 \quad (20)$$

where N_tx is the number of dialysis treatments the patient undergoes per week.

The patient's phosphate binder prescription can be adjusted based on the pre-dialysis serum phosphorus concentration of the patient, C_P_0. If the patient's C_P_0 is between zero and 5.5 mg/dL, that is, within the recommended range, then the phosphate binder prescription is maintained. If the patient's C_P_0 is greater than or equal to 5.5 mg/dL, then the new recommended dosage of phosphate binder, N_PL_REC, using PhosLo® as an example, can be obtained from $$N\_PL\_REC = (P\_di + (nP\_HD\_d/0.75))/25 \quad (21)$$

where nP_HD_d, typically measured in mg/day, is the new daily average amount of phosphorus removed by dialysis. A maximum increase in the prescription of phosphate binder of three pills can be set due to patient safety considerations.

The new daily average amount of phosphorus removed by dialysis, nP_HD_d, can be obtained from $$nP\_HD\_d = nP\_HD*N\_tx/7 \quad (22)$$

where nP_HD, typically measured in mg, is the new amount of phosphorus removed by dialysis, which can be obtained from $$nP\_HD = (-(D\_P*(1-Q\_f/Q\_pw) + Q\_f)*nC\_P\_m)*T/100 \quad (23)$$

where nC_P_m, typically measured in mg/dL, is the new mean serum phosphorus concentration of the patient.

The new mean serum phosphorus concentration of the patient, which accounts for the adjusted phosphate binder dosage, can be obtained from $$nC\_P\_m = 5.5*(1-(1-1.1*(C\_P\_t/C\_P\_0))*(1-\exp(-1.73*KtV\_P))) \quad (24)$$

which differs from Eq. 18 in the leading factor of 5.5, which is the desired target of pre-dialysis serum phosphorus concentration for the patient.

The amount of calcium that needs to be added or removed by diffusion during the hemodialysis treatment including that due to the adjusted phosphorus binder prescription, nCa_HD_D, can be obtained from $$nCa\_HD\_D = -(nCa\_abs\_tx + Avg\_Ca\_HD\_C) + Phys\_Ca\_Acc \quad (25)$$

where nCa_abs_tx, typically measured in mg, is the amount of calcium that a patient has absorbed between treatments, Avg_Ca_HD_C, typically measured in mg, is the average amount of calcium removed convectively by ultrafiltration, and Phys_Ca_Acc, typically measured in mg, is the net accumulation of calcium that a physician can prescribe for a patient who either needs to add or subtract calcium from his system. As discussed above, the net accumulation of calcium for most patients is approximately zero. The average amount of calcium removed convectively by ultrafiltration is initially set to Ca_HD_C and calculated from Eq. 10, and after the patient has had a sufficient number of hemodialysis treatments, Avg_Ca_HD_C is obtained from an average of Ca_HD_C over the previous three months.

The amount of calcium that a patient has absorbed between treatments can be obtained from $$nCa\_abs\_tx = nCa\_abs*7/N\_tx \quad (26)$$

where nCa_abs, typically measured in mg, is the total amount of calcium absorbed by the patient including the phosphorus binder prescription, which can be obtained from $$nCa\_abs = (16.64*\ln(C\_D3) + 19.5)*\ln(Ca\_Di + nCa\_PL) - 38.8*\ln(C\_D3) - 216 \quad (27)$$

where C_D3, typically measured in pg/L (picograms/liter), is the serum concentration of active vitamin $D_3$, Ca_Di, typically measured in mg/day, is the patient's dietary intake of calcium, and nCa_PL, typically measured in mg, is the patient's calcium intake from the newly prescribed dosage of phosphorus binder.

The serum concentration of active vitamin $D_3$, C_D3, can be obtained from $$C\_D3 = 36*Vit\_D \quad (28)$$

where Vit_D, typically measured in mcg/treatment (micrograms/treatment), is the patient's current prescribed dosage of calcitriol (vitamin $D_3$ analog). If the patient has been prescribed Zemplar® or Hectorol® as the vitamin $D_3$ analog, then C_D3 can be obtained from $$C\_D3 = 4.5*Vit\_D \quad (29)$$

The patient's dietary intake of calcium, Ca Di, can be obtained from $$Ca\_Di = 2.25*ePCR + 139 \quad (30)$$

where ePCR, typically measured in mg/day, is the patient's daily intake of protein, obtained from UKM.

The patient's intake of calcium from phosphorus binder, nCa_PL, can be obtained from $$nCa\_PL = 169*N\_PL \quad (31)$$

where N_PL is the number of PhosLo® pills prescribed to the patient.

The calcium concentration in the dialysate that takes into account the patient's intake of calcium from phosphorus binder, nC_Ca_dial, can be obtained from $$nC\_Ca\_dial = 1.12*(nCa\_HD\_D/(D\_Ca*(1-Q\_f/Q\_pe)) + nC\_iCa\_m)/2.0039 \quad (32)$$

where nCa_HD_D is obtained from Eq. 25, and nC_iCa_m is the new mean serum ionized calcium concentration, which can be obtained from $$nC\_iCa\_m = nC\_iCa\_t - ((Avg\_C\_iCa\_0 - nC\_iCa\_t)/(0.012*T))*(\exp(-0.012*T) - 1) \quad (33)$$

where nC_iCa_t, typically measured in mg/dL, is the new serum concentration of ionized calcium post-treatment, and Avg_C_iCa_0, typically measured in mg/dL, is the average pre-treatment serum concentration of ionized calcium. Initially, the average pre-treatment serum concentration of ionized calcium is set equal to C_iCa_0, the patient's measured pre-treatment serum concentration of ionized calcium measured pre-treatment. After the patient has had a sufficient number of hemodialysis treatments, Avg_C_iCa_0 is obtained from an average of C_iCa_0 over the previous three months.

The patient's measured pre-treatment serum concentration of ionized calcium can be obtained from $$C\_iCa\_0 = C\_Ca\_0 * 0.5 \quad (34)$$

where C_Ca_0, typically measured in mg/dL, is the pre-treatment serum concentration of total (bound and ionized) calcium.

The choice of calcium concentration in the dialysate can be influenced by additional patient safety considerations, such as, for example, a patient with a high or low serum total calcium concentration. The commercially available choices of dialysate calcium concentration are typically 2.0, 2.25, 2.5, and 3.0 mEq/L. The dialysate calcium concentration calculated from Eq. 28, nC_Ca_dial, is rounded to the available choices as follows:
a) if nC_Ca_dial≤2.125 mEq/L then Dial_Ca=2.0 mEq/L
b) if 2.126 mEq/L≤nC_Ca_dial≤2.374 mEq/L then Dial_Ca=2.25 mEq/L
c) if nC_Ca_dial≥2.375 mEq/L then Dial_Ca=2.5 mEq/L.

If the patient's pre-dialysis serum phosphorus concentration is within the recommended range and there are no changes suggested in the phosphate binder prescription, but calcium accumulation is suspected, and the calculated nC_Ca_dial is different from the patient's current dialysate prescription, then the change in calcium concentration of the dialysate should be no more than 0.25 mEq/L from the patient's current dialysate prescription. For example, a patient on a 2.5 mEq/L prescription, for whom the calculated nC_Ca_dial is 2.0 mEq/L, will instead be initially suggested a prescription of 2.25 mEq/L. Any patient that is currently prescribed a dialysate calcium concentration of 3.0 mEq/L or above, and for whom the desired calcium accumulation is zero, will be suggested to reduce to 2.5 mEq/L if there are no changes in the phosphate binder prescription, or to reduce to the calculated dialysate calcium concentration, rounded as described above, if there are changes to the phosphate binder prescription.

The recommended serum total (ionized and bound) calcium concentration for a patient is between 8.4 and 9.5 mg/dL. For patient safety considerations, if a patient has a pre-dialysis serum total calcium concentration greater than 9 mg/dL, then increases in dialysate calcium concentration are not recommended. If a patient has a pre-dialysis serum total calcium concentration lower than or equal to 7.99 mg/dL, then a dialysate calcium concentration of 2.5 mEq/L will be used. If a patient has a pre-dialysis serum total calcium concentration of 8.0-8.49 mg/dL, then a dialysate calcium concentration of 2.25 or 2.5 mEq/L will be used, rounded to the nearest choice as described above. If a patient has a pre-dialysis serum total calcium concentration greater than or equal to 8.5 mg/dL, that is, a value within the recommended range, then any of the available choices of dialysate calcium concentration can be used, rounded to the nearest choice as described above.

The flux of calcium into the dialysate stream, $M_{Ca}$, can also be measured directly using calcium ion selective electrodes (ISEs), such as, for example, NOVA 8 (Nova Biomedical). See G. N. Bowers, C. Brassard, and S. F. Sena, *Measurement of Ionized Calcium in Serum with Ion-Selective Electrodes: A Mature Technology That Can Meet the Daily Service Needs*, 32 Clinical Chemistry pp. 1437-1447 (1986).

Figure 4:
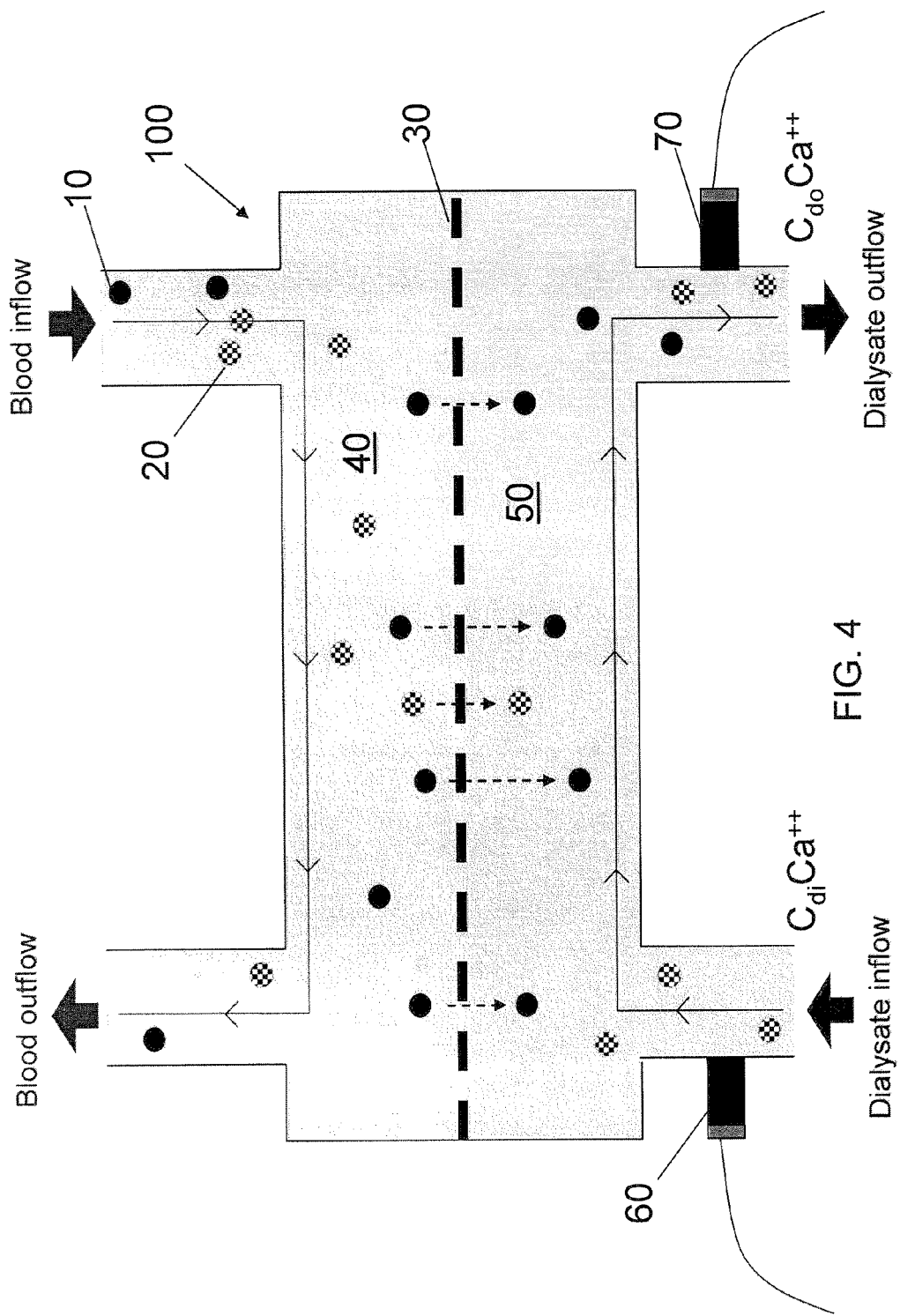
FIG. 4 is a representation of a dialysis apparatus, including calcium ion selective electrodes for measurement of inlet and outlet calcium concentration of the dialysate solution.

Turning now to FIG. 4, blood flowing into dialysis apparatus 100 contains uremic toxins 10 and calcium ions 20 that move across dialysis membrane 30 by diffusive and convective transport, from the blood side 40 to the dialysate side 50. The diffusive transport results from a concentration gradient between the blood side 40 and the dialysate side 50. The convective transport results from fluid movement across the dialysis membrane 30, driven by hydrostatic forces. The inlet concentration of ionized calcium in the dialysate, $C_{di}Ca^{++}$, can be measured by calcium ISE 60. The outlet concentration of ionized calcium in the dialysate, $C_{do}Ca^{++}$, can be measured by calcium ISE 70. The instantaneous intradialytic calcium mass balance, $M_{inst}Ca^{++}$ can be obtained from $$M_{inst}Ca^{++} = C_{di}Ca^{++} * Q_{di} - C_{do}Ca^{++} * (Q_{di} + Q_f) \quad (35)$$

where $Q_{di}$, typically measured in ml/min, is the dialysate flow rate. The measured intradialytic calcium mass balance over the entire dialysis treatment, $_{meas}Ca_{MB}HD$, can be obtained from $$_{meas}Ca_{MB}HD = M_{inst}Ca^{++} * t_d \quad (36)$$

which can be compared to the model result obtained from Eq. 2.

The dialysate solution containing the adjusted calcium concentration is then used in performing a dialysis treatment of the patient. The dialysis treatment can be a hemodialysis treatment, employing dialyzers known in the art (e.g., Fresenius Medical Care, Baxter Healthcare). A preferred hemodialysis treatment can employ a high flux dialyzer (e.g., Fresenius Medical Care 180NR) that can remove larger amounts of phosphorus during the dialysis treatment, thus lowering the need for administering phosphate binder to the patient. The model can also be employed in treating patients with continuous renal replacement therapies, or with low flux dialyzers.

EXEMPLIFICATION

Example 1

Nine hemodialysis patients (Pt) were monitored during 32 dialyses with high flux dialyzers (180NR), blood & dialysate flows of 400 ml/min and 500 ml/min, respectively, and $C_{di}Ca^{++}$ of 1.75 to 3.0 mEq/L. Data measured: plasma $Ca^{++}$ ($C_pCa^{++Meas}$) at t=0, 60 min and end dialysis; $C_{di}Ca^{++}$ and $C_{do}Ca^{++}$ (outflow) every 10 min with NOVA 8 (calcium ion sensitive electrode) in 2 Pts ($D_{10}$) and by dialysate collection in 7 Pts ($D_{COL}$). A previously described Ca Kinetic model (Blood Purifi 25:139-149, 2007) was used to calculate: convective and diffusive Ca flux ($J_CCa$, $J_DCa$); mobilization or sequestration of Ca ($M_{Ca}$) in the Miscible Calcium Pool (MCP); $Ca^{++}$ mass balance ($Ca_{MB}$) and $C_pCa$ ($C_pCa^{++Calc}$) every 10 min in $D_{10}$ and thrice in $D_{COL}$. The $D_{10}$ model was validated from comparison of $C_pCa^{++Meas}$ to the values for $C_pCa^{++Calc}$ (calculated from Ca flux and dialysance). $Ca_{MB}$ was calculated as function of ($C_{di}Ca^{++} - C_{pi}Ca^{++}$) and a Miscible Calcium Pool Buffer Coefficient ($K_{MP}$) as $K_{MP} = M_{Ca}/(M_{Ca} + J_dCa)$, where the $K_{MP}$ expresses the fraction of $J_dCa$ which comes from the MCP rather than plasma and extracellular fluid ($\Delta Ca_{ECW}$). In the notation of Eq. 1, $K_{MP} = |Ca\_MP|/(|Ca\_MP| + |Ca\_EC\_D|)$. The three $C_pCa^{++Meas}$ values were fit to a continuous function where $C_pCa^{++Meas}$ approached the end dialysis value as an asymptote so $C_pCa^{++Meas}$ could be compared to $C_pCa^{++Calc}$ every 10 min.

Figure 5:
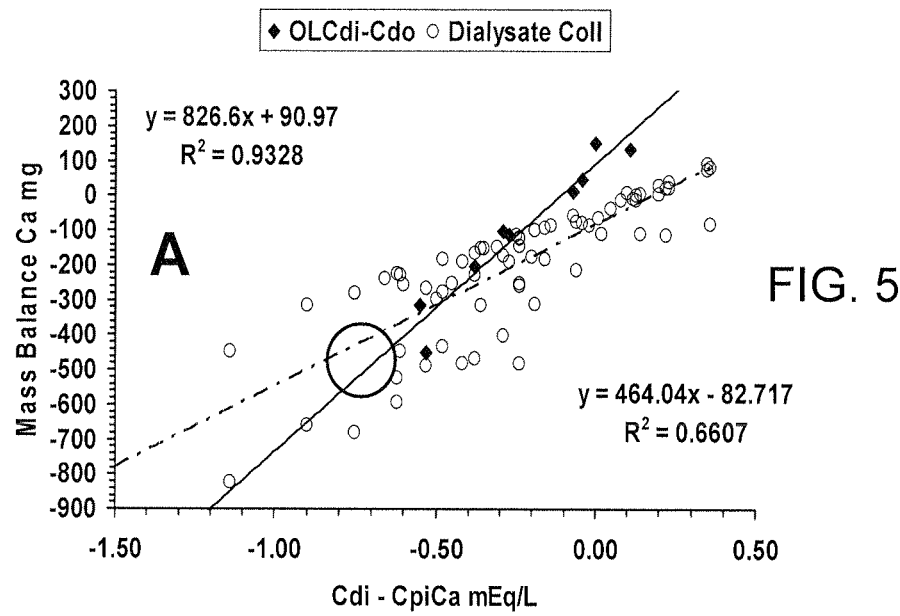
FIG. 5 is a graph of ($C_{di}Ca^{++} - C_{pt}Ca^{++}$) as a function of intradialytic calcium mass balance.
Figure 6:
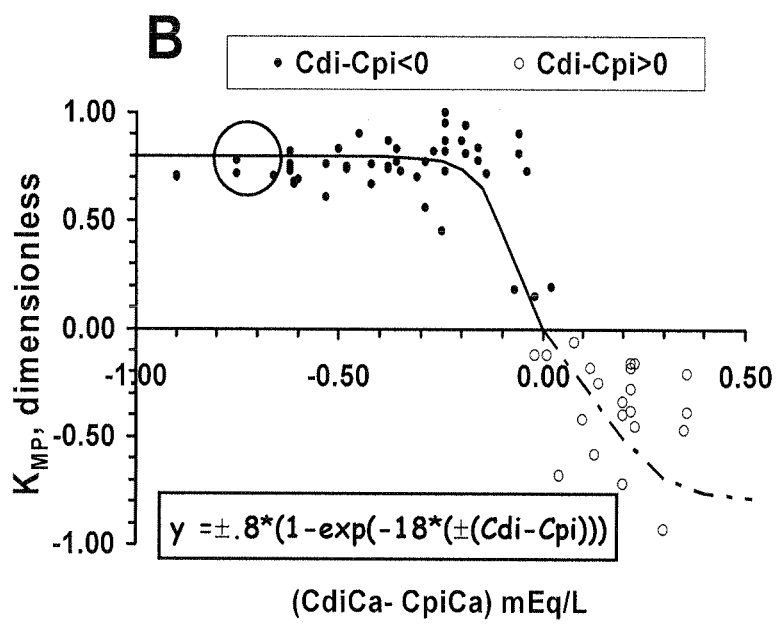
FIG. 6 is a graph of ($C_{di}Ca^{++} - C_{pt}Ca^{++}$) as a function of $K_{MP}$.

Correlation of $C_pCa^{++Meas}$ to $C_pCa^{++calc}$: In Pt1: $C_pCa^{++Meas} = 0.88 * C_pCa^{++Calc} + 0.88$, n=62, $R^2 = 0.94$. In Pt2:

$C_pCa^{++Meas}=76*C_pCa^{++Calc}+1.7$, n=91, $R^2$=0.91. The relationship of $Ca_{MB}$ to $(C_{di}Ca^{++}-C_{pi}Ca^{++})$ is shown in FIG. 5. The correlations are very good for both $D_{10}$ and $D_{COL}$ and very high for $D_{10}$. The relationship of $K_{MP}$ to $(C_{di}Ca^{++}-C_{pi}Ca^{++})$, shown in FIG. 6, indicates that the bulk of diffusive Ca flux is derived from the MCP rather than $Ca_{ECW}$ with both positive and negative gradients. With a gradient=−0.75 mEq/L, Ca removal is 450 to 550 mg of which 80% is derived from the MCP.

These data provide the first reported prospective quantification of the magnitude of MCP buffering of change in $Ca_{ECW}$ over a wide range of dialyzer Ca diffusion gradients and show that 80% of diffusive flux comes from the MCP. The very high correlation of $Ca_{MB}$ to $(C_{di}Ca^{++}-C_{pi}Ca^{++})$ with $D_{10}$ suggests that deployment of $C_{di}Ca^{++}$ and $C_{do}Ca^{++}$ electrodes in the inlet/outlet streams could provide reliable real time on line monitoring of $Ca_{MB}$. $J_dCa$ and $K_{MP}$ could also be calculated from measurement of pre and post dialysis $C_pCa^{++}$ with known $C_{di}Ca^{++}$ and Ca dialysance.

In conclusion, 80% of diffusive dialyzer Ca flux was found to be buffered by the MCP which greatly reduces the magnitude of change in $\Delta Ca_{ECW}$ during sizeable amounts of Ca removal. In addition, Ca removal of about 500 mg was achieved with $(C_{di}Ca^{++}-C_{pi}Ca^{++})=-0.75$ mEq/L.

Example 2

Figure 7:
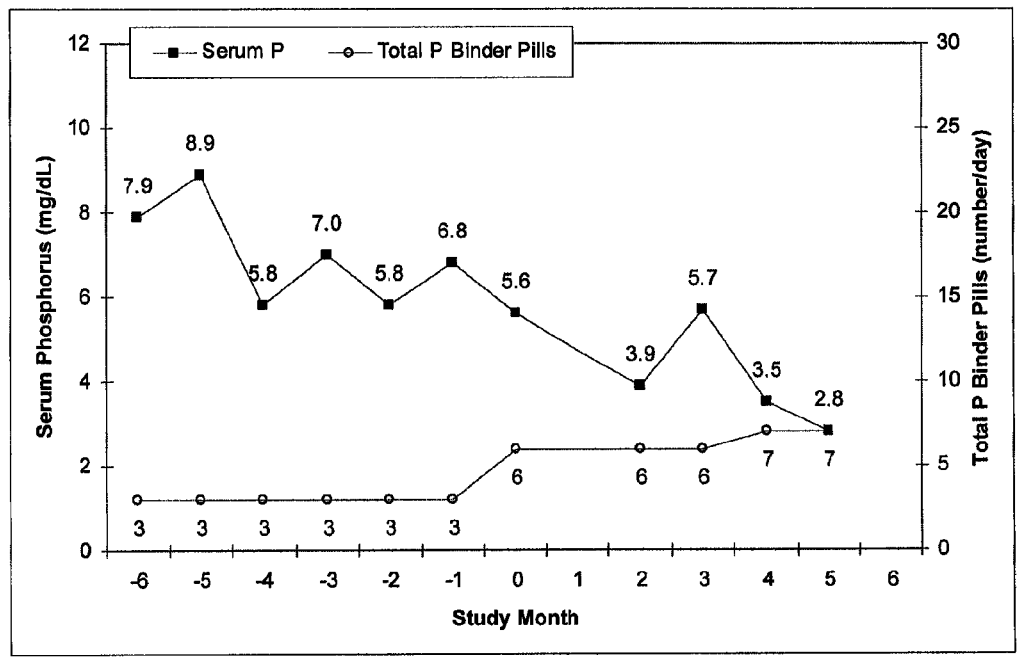
FIG. 7 is a graph of serum phosphorus concentration and total prescribed number of phosphorus binder pills as a function of time for Patient 1.
Figure 8:
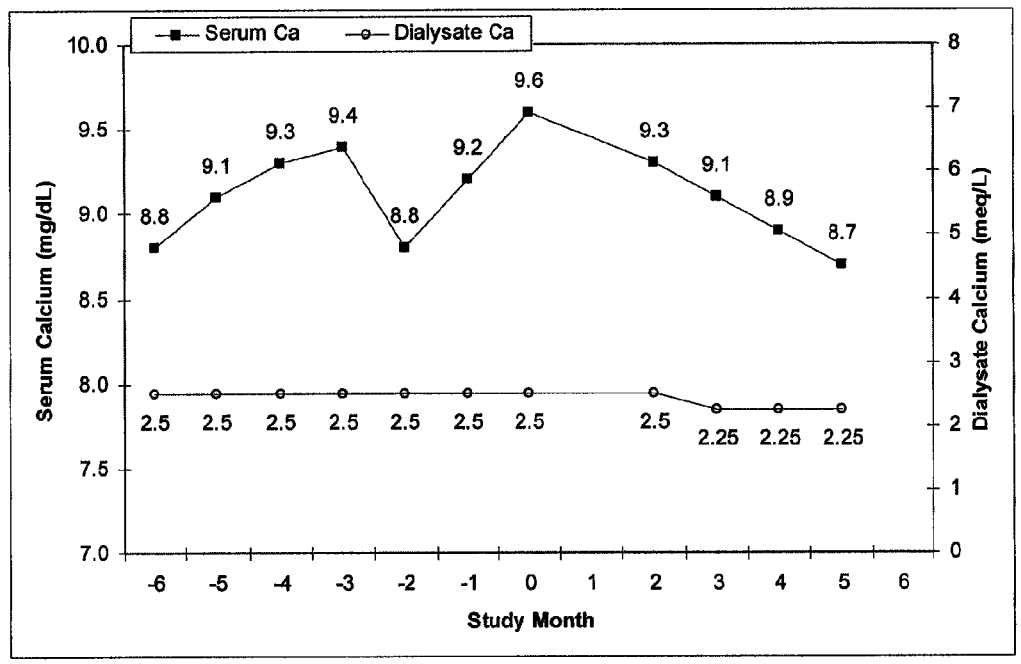
FIG. 8 is a graph of serum calcium concentration and dialysate calcium concentration as a function of time for Patient 1.

Patient 1 was a 53 year old diabetic, African-American male with a dialysis vintage of 19 months. Prior to use of PKM modeling, the 6-month, 3-month, and 1-month average serum P was 7.0, 6.5, and 6.8 mg/dL, respectively. All of these values are outside the recommended guidelines of 3.5-5.5 mg/dL. Prior to use of PKM modeling, the 6-month average serum Ca was 9.1 mg/dL, which falls within the recommended guidelines of 8.4-9.5 mg/dL. In the 6 months prior to the study, Patient 1 was prescribed 3 (800 mg) Renagel® tablets per day. Once per month for 6 months (study months 0-5), input values were collected for the PKM model and recommended binder prescription and dialysate calcium concentrations were calculated. As illustrated in FIG. 7, during the study period, Patient 1's binder prescription was increased to 6 and then 7 PhosLo® pills (667 mg per pill) per day in order to bring serum P level down to the recommended guidelines. Additionally, as illustrated in FIG. 8, the dialysate calcium concentration was lowered from 2.5 to 2.25 meq/L to avoid increased absorption of calcium. For the 6 month study period, average serum P was 4.0 mg/dL and average serum Ca was 9.0 mg/dL. Both serum P and Ca fell within recommended guidelines for the study period.

Example 3

Figure 9:
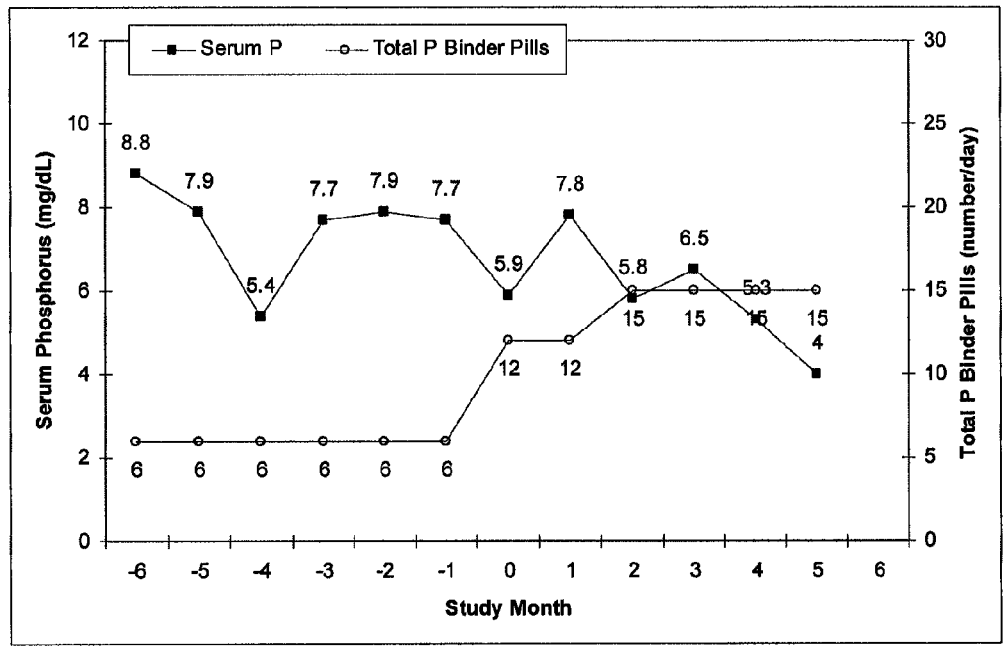
FIG. 9 is a graph of serum phosphorus concentration and total prescribed number of phosphorus binder pills as a function of time for Patient 2.
Figure 10:
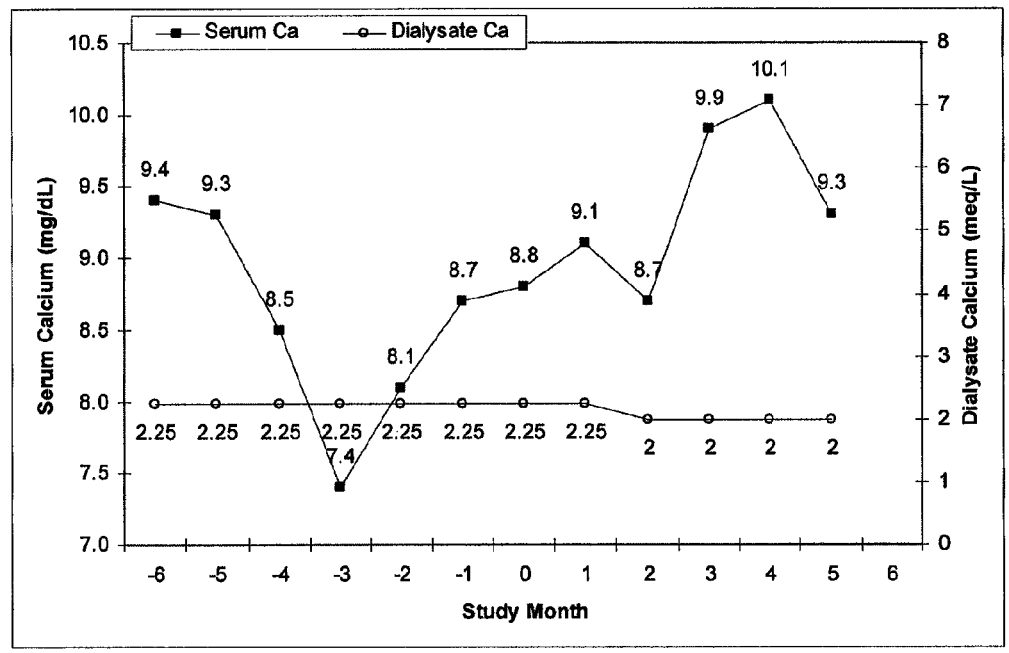
FIG. 10 is a graph of serum calcium concentration and dialysate calcium concentration as a function of time for Patient 2.

Patient 2 was a 61 year old African-American male with a dialysis vintage of 41 months. Prior to use of PKM modeling, the 6-month, 3-month, and 1-month average serum P was 7.6, 7.8, and 7.7 mg/dL, respectively. All of these values are outside the recommended guidelines of 3.5-5.5 mg/dL. Prior to use of PKM modeling, the 6-month average serum Ca was 8.6 mg/dL, which falls within the recommended guidelines of 8.4-9.5 mg/dL. In the 6 months prior to the study, Patient 2 was prescribed 6 PhosLo® tablets per day. Once per month for 6 months (study months 0-5), input values were collected for the PKM model and recommended binder prescription and dialysate calcium concentrations were calculated. As illustrated in FIG. 9, during the study period, Patient 2's binder prescription was increased to 12 and then 15 PhosLo® pills per day in order to bring serum P level down to the recommended guidelines. Additionally, as illustrated in FIG. 10, the dialysate calcium concentration was lowered from 2.25 to 2.0 meq/L to avoid increased absorption of calcium. For the 6 month study period, average serum P was 5.9 mg/dL and average serum Ca was 9.3 mg/dL. Average serum P fell by 22% although did not meet target guidelines. Average serum Ca was within recommended guidelines for the study period. The average serum P for the last 3 months of the study was 5.3 mg/dL. Continued observation in the study would likely continue to result in serum P value within the recommended guidelines.

Example 4

Figure 11:
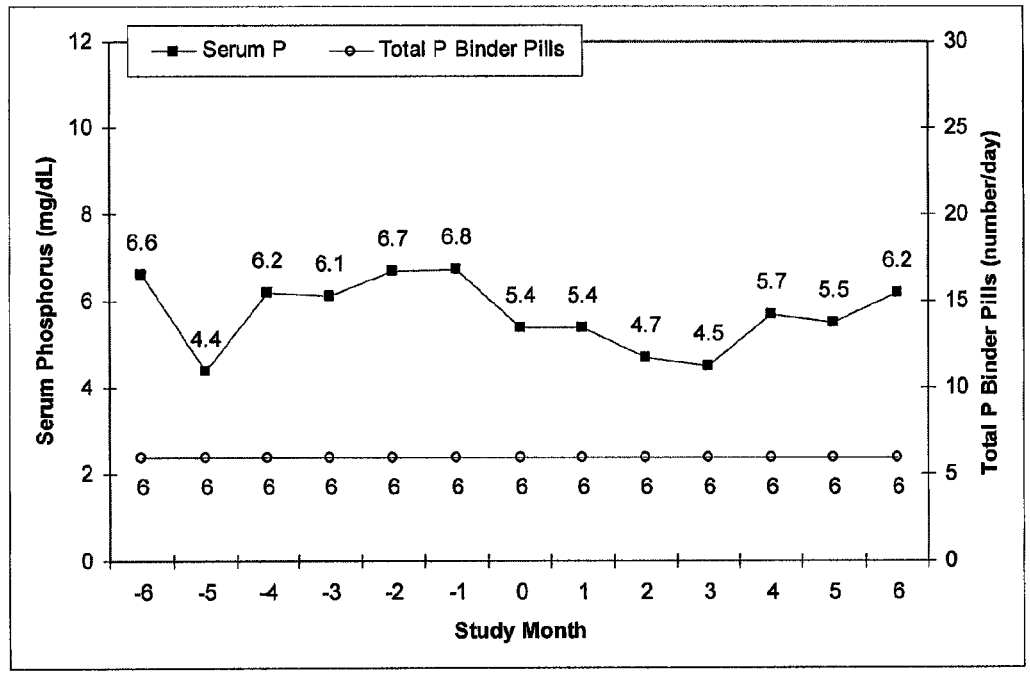
FIG. 11 is a graph of serum phosphorus concentration and total prescribed number of phosphorus binder pills as a function of time for Patient 3.
Figure 12:
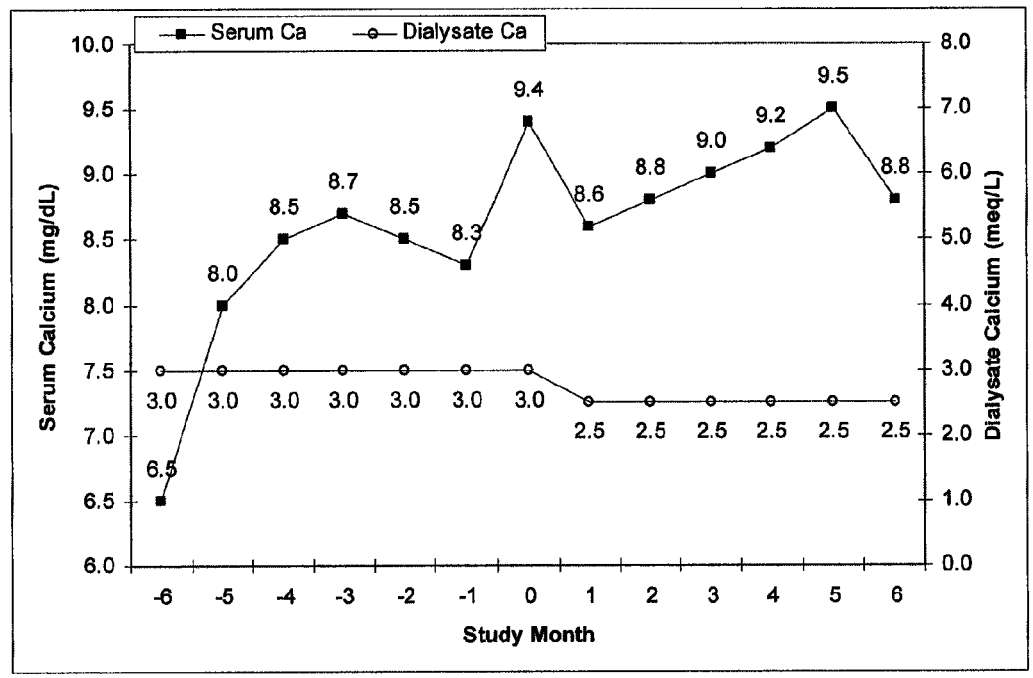
FIG. 12 is a graph of serum calcium concentration and dialysate calcium concentration as a function of time for Patient 3.

Patient 3 was a 72 year old diabetic, white female with a dialysis vintage of 22 months. Prior to use of PKM modeling, the 6-month, 3-month, and 1-month average serum P was 6.2, 6.6, and 6.8 mg/dL, respectively. All of these values are outside the recommended guidelines of 3.5-5.5 mg/dL. Prior to use of PKM modeling, the 6-month average serum Ca was 8.1 mg/dL, which falls below the recommended guidelines of 8.4-9.5 mg/dL. As illustrated in FIG. 11, in the 6 months prior to the study, Patient 3 was prescribed 6 PhosLo® tablets per day. Once per month for 7 months (study months 0-6), input values were collected for the PKM model and recommended binder prescription and dialysate calcium concentrations were calculated. During the study period, Patient 1's binder prescription was maintained at 6 PhosLo® pills per day. As illustrated in FIG. 12, the dialysate calcium concentration was lowered from 3.0 to 2.5 meq/L. For the 6 month study period, average serum P was 5.3 mg/dL and average serum Ca was 9.0 mg/dL. Both serum P and Ca fell within recommended guidelines for the study period. Although the phosphorus binder dosage was not increased, the decrease in serum phosphorus concentration may be attributed to increased patient awareness of diet and prescriptions as a result of additional education and monitoring provided by the study program.

Example 5

Figure 13:
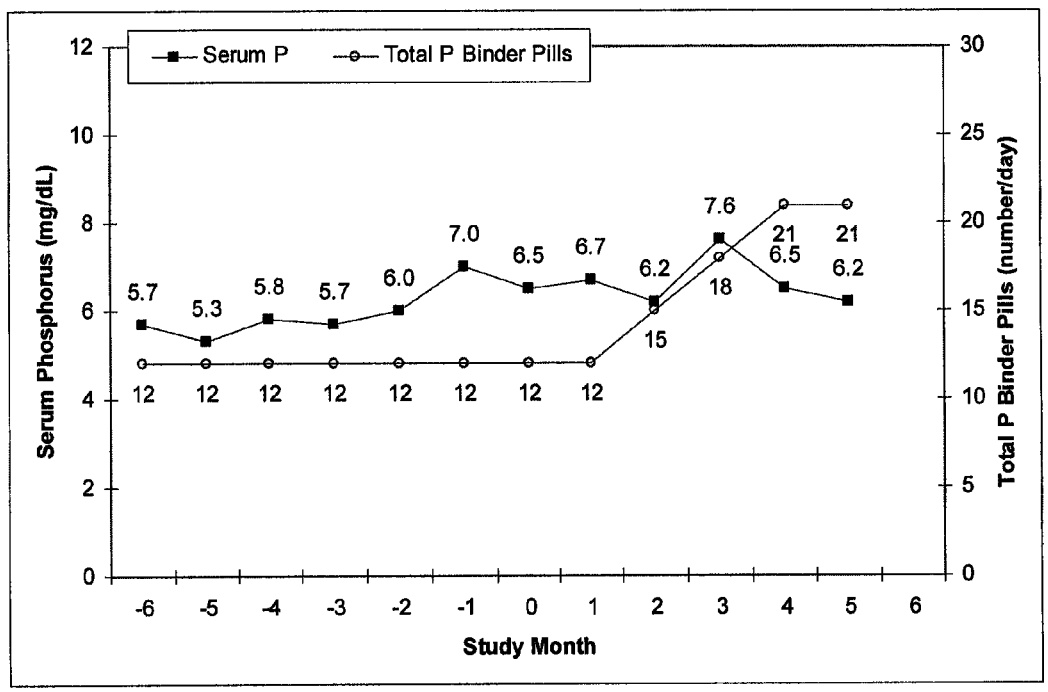
FIG. 13 is a graph of serum phosphorus concentration and total prescribed number of phosphorus binder pills as a function of time for Patient 4.
Figure 14:
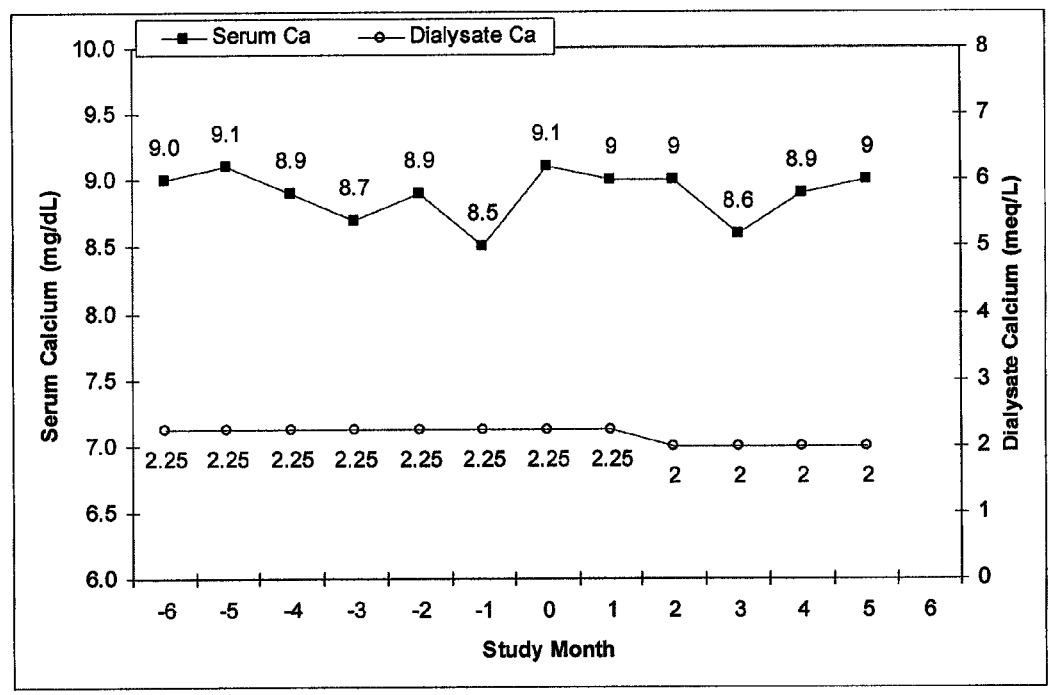
FIG. 14 is a graph of serum calcium concentration and dialysate calcium concentration as a function of time for Patient 4.

Patient 4 was a 63 year old diabetic, white male with a dialysis vintage of 40 months. Prior to use of PKM modeling, the 6-month, 3-month, and 1-month average serum P was 5.9, 6.2, and 7.0 mg/dL, respectively. All of these values are outside the recommended guidelines of 3.5-5.5 mg/dL. Prior to use of PKM modeling, the 6-month average serum Ca was 8.9 mg/dL, which falls within the recommended guidelines of 8.4-9.5 mg/dL. In the 6 months prior to the study, Patient 4 was prescribed 12 PhosLo® tablets per day. Once per month for 6 months (study months 0-5), input values were collected for the PKM model and recommended binder prescription and dialysate calcium concentrations were calculated. As illustrated in FIG. 13, during the study period, Patient 4's binder prescription was increased steadily from 12 to 21 PhosLo® pills per day in an attempt to bring serum P level down within the recommended guidelines. Additionally, as illustrated in FIG. 14, the dialysate calcium concentration was lowered from 2.25 to 2.0 meq/L to avoid increased absorption of calcium. For the 6 month study period, average serum P was 6.6 mg/dL and average serum Ca was 8.9 mg/dL. Serum Ca was within recommended guidelines for the study period; however serum P did reach the recommended range. Although the PKM model can suggest a phosphorus binder dosage to lower the patient's serum phosphorus concentration, if patients are non-compliant with this prescription or recommended diet, then the serum phosphorus concentration will not be lowered.

The relevant teachings of all patents, published applications and references cited herein are incorporated by reference in their entirety.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of determining a dosage of phosphorus binder for a patient undergoing dialysis treatment to achieve a pre-dialysis serum phosphorus concentration within a desired concentration range while achieving a desired net accumulation of calcium, comprising:
   a) calculating an intradialytic calcium mass balance for the patient;
   b) calculating an intradialytic phosphorus mass balance for the patient;
   c) establishing a phosphorus kinetic model using the intradialytic calcium mass balance and intradialytic phosphorus mass balance determined in a) and b);
   d) using the phosphorus kinetic model to determine a dosage of phosphorus binder that will achieve a pre-dialysis serum phosphorus concentration of the patient that is within the desired concentration range while accounting for the change in the amount of phosphorus which will be removed by the dialysis treatment when the pre-dialysis serum phosphorus concentration of the patient is within the desired concentration range;
   e) using the phosphorus kinetic model to determine a dialysate calcium concentration that will result in the desired net accumulation of calcium in the patient over a complete dialysis cycle; and
   f) dialyzing the patient with a dialysate containing a calcium concentration based upon the concentration determined in step e).

2. The method of claim 1, wherein the patient has at least one disease or condition selected from the group consisting of renal insufficiency, renal failure, kidney disease, hyperphosphatemia, hypercalcemia, hypocalcemia, end-stage renal disease, and cancer.

3. The method of claim 1, wherein the dialysate calcium concentration is determined from a calcium mass balance over the complete dialysis cycle.

4. The method of claim 3, wherein the desired net accumulation of calcium is approximately zero.

5. The method of claim 1, wherein the desired range for the pre-dialysis serum phosphorus concentration of the patient is between about 3.5 mg/dL and about 5.5 mg/dL.

6. The method of claim 1, wherein the dialysate calcium concentration is determined by considering additional patient safety considerations in changing the dialysate calcium concentration from one dialysis treatment to the next.

* * * * *